United States Patent [19]

Nakamura et al.

[11] Patent Number: 5,175,307

[45] Date of Patent: Dec. 29, 1992

[54] DIACETYLENE COMPOUND HAVING DOUBLE BOND AND SHAPED ARTICLE THEREOF

[75] Inventors: Katsuyuki Nakamura; Satoru Yamazaki; Jinichiro Kato; Kensaku Tokushige, all of Nobeoka, Japan

[73] Assignee: Agency of Industrial Science & Technology, Tokyo, Japan

[21] Appl. No.: 618,997

[22] Filed: Nov. 28, 1990

Related U.S. Application Data

[63] Continuation of Ser. No. 484,005, Feb. 23, 1990, Pat. No. 4,987,257, which is a continuation of Ser. No. 363,330, Jun. 7, 1989, abandoned, which is a continuation of Ser. No. 32,445, Mar. 31, 1987, abandoned.

[30] Foreign Application Priority Data

May 16, 1986 [JP] Japan ............................. 61-110908
Jun. 6, 1986 [JP] Japan ............................. 61-130101

[51] Int. Cl.$^5$ .................................................. C07D 209/48
[52] U.S. Cl. ........................................ 548/462; 548/545; 548/546
[58] Field of Search .......................... 548/462, 545, 546

[56] References Cited

U.S. PATENT DOCUMENTS

| | | | |
|---|---|---|---|
| 3,472,868 | 10/1969 | Ber et al. | 548/545 |
| 3,773,797 | 11/1973 | Chodnekar et al. | 549/1 X |
| 3,940,425 | 2/1976 | Eiter | 564/160 |
| 4,225,498 | 9/1980 | Baudouin et al. | 548/462 |
| 4,321,198 | 3/1982 | D'Alelio et al. | 548/462 |
| 4,331,794 | 5/1982 | D'Alelio et al. | 548/462 |
| 4,376,206 | 3/1983 | Oba et al. | 548/546 |

FOREIGN PATENT DOCUMENTS

| | | | |
|---|---|---|---|
| 60-38352 | 2/1985 | Japan | 564/55 |
| 2267248 | 11/1987 | Japan | 564/159 |
| 3068549 | 3/1988 | Japan | 564/155 |
| 1-186852 | 7/1989 | Japan | 564/156 |

OTHER PUBLICATIONS

Chemical Abstracts 107(15): 133877r, Oct. 12, 1987.
Reimlinger, Liebigs Ann. Chem. 713, 113-8 (1968).
Chemical Abstracts 86:89126s (1977).
Chemical Abstracts 72:66330r (1970).

*Primary Examiner*—Carolyn Elmore
*Assistant Examiner*—Shailendra Kumar
*Attorney, Agent, or Firm*—Cushman, Darby & Cushman

[57] ABSTRACT

Disclosed is a diacetylene compound comprising, as structural units, (a) at least one member selected from diacetylene group-containing organic groups of the formulae (I) and (II):

$$R^I-C\equiv C-C\equiv C-R^{II}- \qquad (I)$$

and $$-R^{III}-C\equiv C-C\equiv C-R^{IV}- \qquad (II)$$

wherein $R^I$ is hydrogen or a (C1-16) monovalent organic group, and $R^{II}$, $R^{III}$ and $R^{IV}$ are a (C1-13) divalent organic group, (b) at least one organic group having at least one carbon-to-carbon double bond, and (c) at least one connecting group connecting the units (a) and (b), which connecting group is selected from amide, imide, ester, ether, amino, imino, urethane, sulfonyl and carbonyl bonds. A cured shaped article made of this compound exhibits isotropically a high elastic modulus and has excellent mechanical properties.

4 Claims, 2 Drawing Sheets

DIACETYLENE COMPOUND HAVING DOUBLE BOND AND SHAPED ARTICLE THEREOF

This is a continuation of application Ser. No. 07/484,005, filed Feb. 23, 1990, now U.S. Pat. No. 4,987,257, which is a continuation of Ser. No. 07/363,330, filed Jun. 7, 1989, now abandoned, which is a continuation of Ser. No. 07/032,445 filed Mar. 31, 1987, now abandoned.

BACKGROUND OF THE INVENTION (1) Field of the Invention

The present invention relates to a diacetylene compound having at least one double bond, which has excellent curing reactivity and provides a shaped article having a high elastic modulus, and to a shaped article thereof.

(2) Description of the Related Art

As the thermosetting resin, a phenolic resin, an epoxy resin, an unsaturated polyester resin and other resin are known. However, cured shaped articles obtained from these resins have an elastic modulus of 4 to 5 GPa at highest. Therefore, when these resins are utilized as materials having high strength and high elastic modulus, they are used as fiber-reinforced composite materials.

Recently, an imide material having an ethynyl group or a mixed material comprising an imide compound having a diacetylene bond at the terminal and a dienophile compound has been investigated as a new curing material, and possibilities of this new curing resin have been examined (see U.S. Pat. No. 4,311,601, 4,402,879 and 4,405,786). However, the elastic modulus of a cured shaped article of this curing resin is not superior to that of a cured shaped article of a conventional curing resin.

Separately, a fiber having a high elastic modulus has been manufactured on an industrial scale by highly orienting a non-curable linear polymer. For example, there can be mentioned a gel-spun fibrous product of polyethylene and a liquid crystal-spun fibrous product of poly-p-phenylene terephthalamide.

In these materials, however, a high elastic modulus is manifested in the orientation direction but the elastic modulus is low in the direction rectangular to the orientation direction.

As an interesting example, there can be mentioned an investigation in which a whisker polymer close to a single crystal is synthesized by solid-phase reaction of a diacetylene compound having urethane bonds, sulfonyl bonds or other bonds [see Polymer, 24, 1023 (1983); Journal of Polymer Science, Polymer Physics Ed. 17, 569 (1979); and Report 1984 (Order No. AD-A140912)]. However, as in case of the above-mentioned highly oriented linear polymer, a high elastic modulus can be manifested only in one direction and it is impossible to manifest high strength and elastic modulus two-dimensionally or three-dimensionally.

SUMMARY OF THE INVENTION

It is the primary object of the present invention to provide a curable compound which has a high reactivity and is capable of providing a cured shaped article having a high elastic modulus isotropically and excellent mechanical properties.

In accordance with the present invention, there is provided a diacetylene compound comprising, as structural units, (a) at least one member selected from diacetylene group-containing organic groups represented by the following general formulae (I) and (II):

and

wherein $R^I$ represents a hydrogen atom or a monovalent organic group having 1 to 16 carbon atoms, and $R^{II}$, $R^{III}$ and $R^{IV}$ independently represent a divalent organic group having 1 to 13 carbon atoms, (b) at least one organic group having at least one carbon-to-carbon double bond, and (c) at least one connecting group connecting the structural units (a) and (b), which is selected from an amide bond, an imide bond, an ester bond, an ether bond, an amino bond, an imino bond, a urethane bond, a sulfonyl bond and a carbonyl bond.

Furthermore, a shaped article made of the diacetylene compound mentioned above is provided according to the present invention.

DESCRIPTION OF THE PREFERRED EMBODIMENTS

Figure 1:
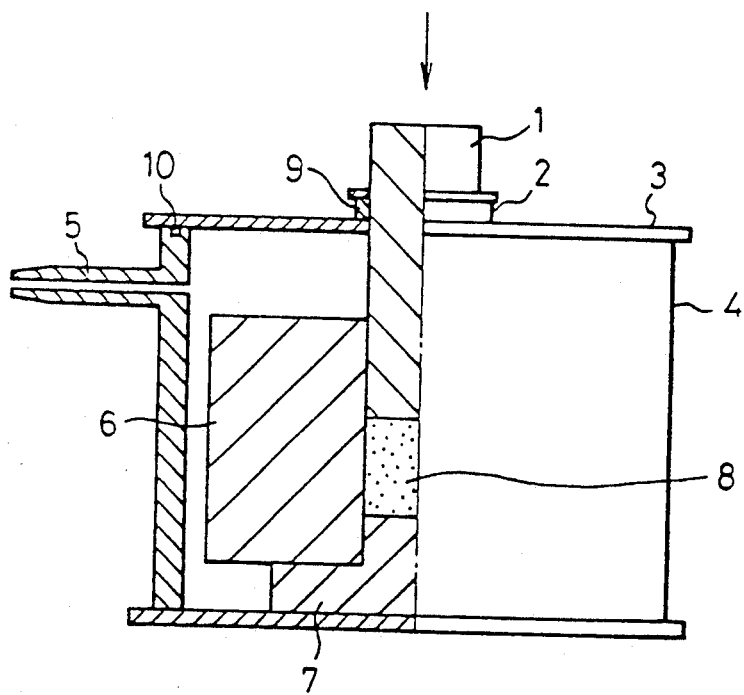
FIG. 1 is a partially cut-out sectional view of a molding machine used for making the compound of the present invention into a shaped article.

In the present invention, $R^I$ in the general formula (I) represents a monovalent organic group having 1 to 16 carbon atoms or a hydrogen atom. As examples of $R^I$, there can be mentioned H—, $CH_3$—, $C_2H_5$—, $C_3H_7$—, $(CH_3)_2CH$—, $(CH_3)_3C$—,

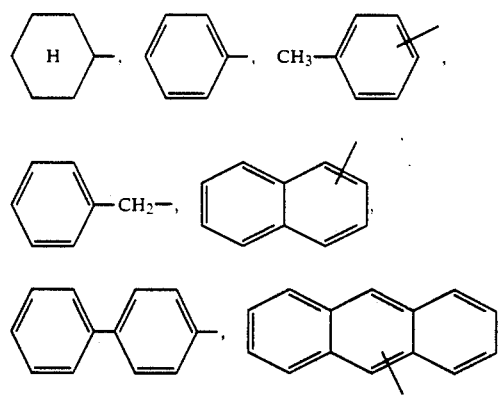

and

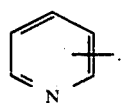

The organic group $R^I$ may contain a divalent connecting group such as an ether bond, an ester bond, an amide bond, an imide bond, an amino bond, an imino bond or a urethane bond. As examples of $R^I$ of this type, there can be mentioned

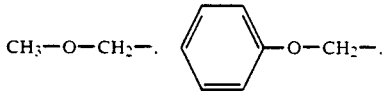

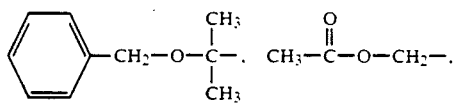

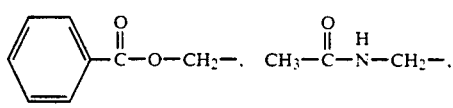

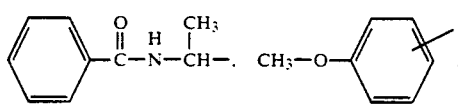

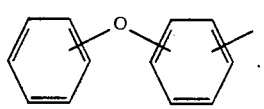

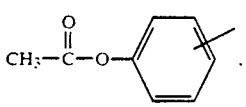

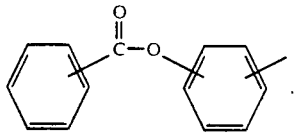

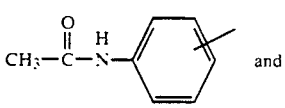

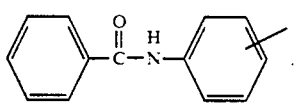

Some or all of the hydrogen atoms of the organic group $R^I$ may be substituted by a nitro group, a hydroxyl group, a cyano group, a carboxyl group, an amino group, a halogen atom or other substituents.

In the present invention, $R^{II}$, $R^{III}$ and $R^{IV}$, which may be the same or different, represent a divalent organic group having 1 to 13 carbon atoms. For example, there can be mentioned aliphatic and alicyclic organic groups such as —CH$_2$—, —C$_2$H$_4$—, —C$_3$H$_6$—,

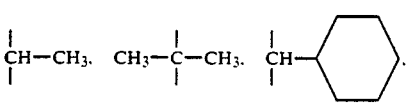

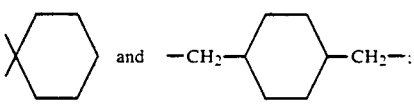

-continued aromatic groups such as 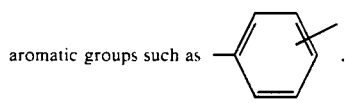

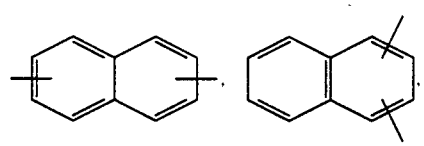

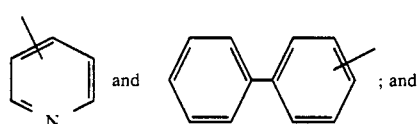

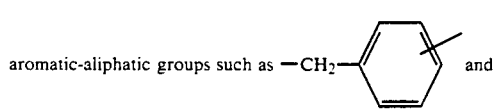

aromatic-aliphatic groups such as 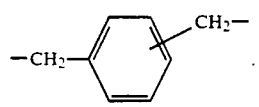 and

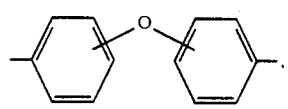

Some or all of the hydrogen atoms of these organic groups may be substituted by a nitro group, a hydroxyl group, a cyano group, a carboxyl group, an amino group, a halogen atom or other substituents.

The organic group $R^{II}$, $R^{III}$ and $R^{IV}$ may have an ether bond, a sulfonyl bond, an ester bond or a carbonyl bond. For example there can be mentioned

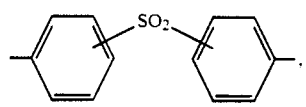

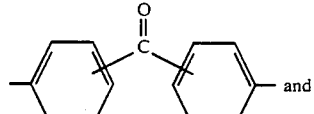

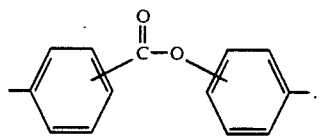

$R^{II}$, $R^{III}$ and may be any of the foregoing groups. However, in view of the curing reactivity and the easiness of the synthesis, —CH$_2$— and

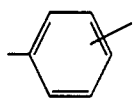

are preferred.

In the present invention. the organic group (b) having at least one carbon-to-carbon double bond is generally a monovalent or polyvalent organic group having 1 to 20 carbon atoms and at least one carbon-to-carbon double bond.

For example, there can be mentioned groups comprising at least one carbon-to-carbon double bond and an aliphatic group, such as $H_2C=CH-$,

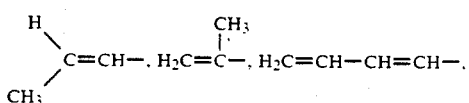

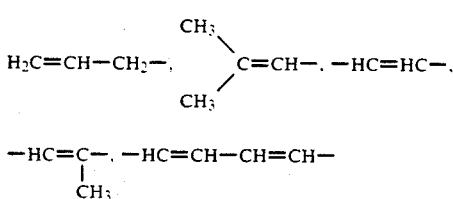

and $-CH_2-HC=CH-CH_2-$; groups comprising at least one double bond and an aromatic group, such as

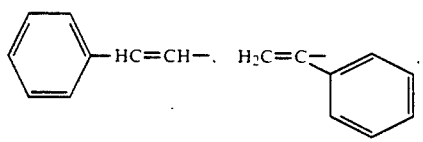

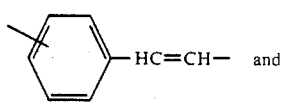

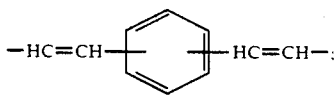

and groups having at least one double bond included in a ring structure, such as

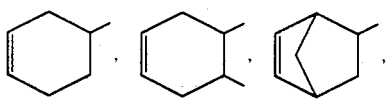

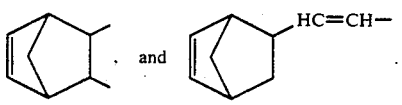

Some or all of the hydrogen atoms of these organic groups (c) may be substituted by a nitro group, a hydroxyl group, a cyano group, a carboxyl group, an amino group, a halogen atom or other substituents.

Among these double bond-containing groups, in view of the reactivity,

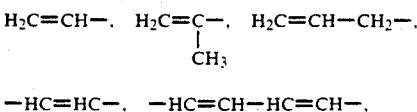

$-HC=HC-$, $-HC=CH-HC=CH-$,

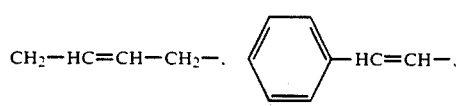

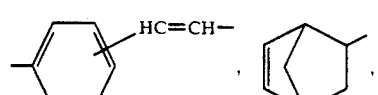

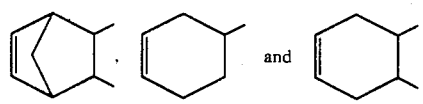

are preferred.

The diacetylene compound of the present invention comprises as another structural unit a connecting (c) group connecting the above-mentioned diacetylene group-containing organic group (a) and carbon-to-carbon double bond-containing organic group (b). As the connecting group, there can be mentioned an ether bond $-O-$,

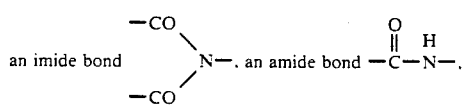

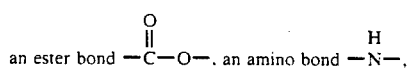

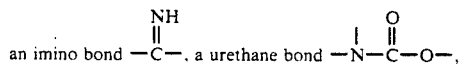

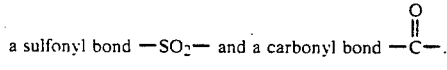

The oxygen atom constituting the connecting group may be substituted by a sulfur atom. Any of the foregoing connecting groups may be used. Furthermore, two or more of the connecting groups, may be used in combination.

Among these connecting groups, in view of the balance between the processability and the curing reactivity, an amide bond, an ester bond, a sulfonyl bond, a carbonyl bond and an ether bond are preferred. Furthermore, an imide bond is preferred in view of the heat resistance of the cured shaped article. An amide bond and an ester bond are especially preferred.

The diacetylene compound of the present invention is a compound in which the above-mentioned diacetylene group-containing organic group (a) and carbon-to-carbon double bond-containing organic group (b) are connected in one molecule through the connecting group((c). The numbers of the diacetylene group-containing organic group, carbon-to-carbon double bond-containing organic group and connecting group present in one molecule are not particularly critical. For example, the diacetylene compound may be a compound containing one each of the foregoing groups or a compound containing two or more of these groups. In the case where the diacetylene group-containing group, carbon-to-carbon double bond-containing organic group and connecting group are contained as repeating units, the units of each group (c) may be the same or different.

In the diacetylene compound of the present invention, the ratio of the diacetylene group-containing organic group (a) to the carbon-to-carbon double bond-containing organic group (b) is not particularly critical. In view of the curing reactivity, it is preferred that the molar ratio of the diacetylene group-containing organic group (a) to the carbon-to-carbon double bond-containing group (b) be in the range of from 0.2 to 5, and it is especially preferred that this molar ratio be in the range of from 0.5 to 2, because the curing reactivity is most prominent and the elastic modulus of the cured shaped article is highly improved.

Examples of the diacetylene compounds of the present invention are as follows:

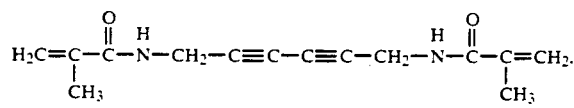

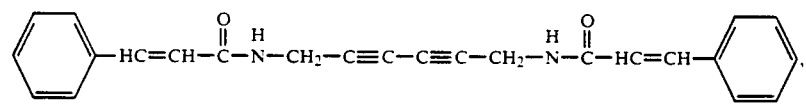

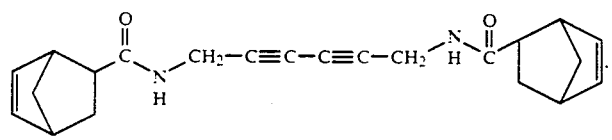

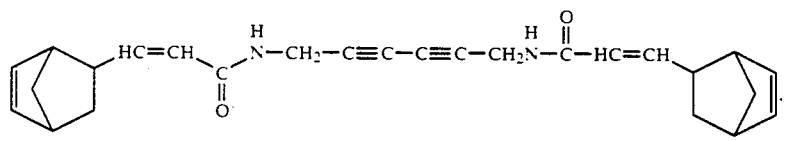

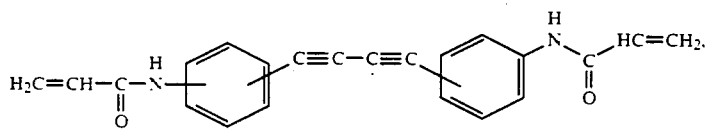

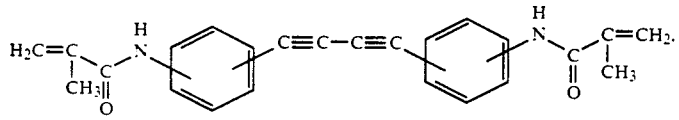

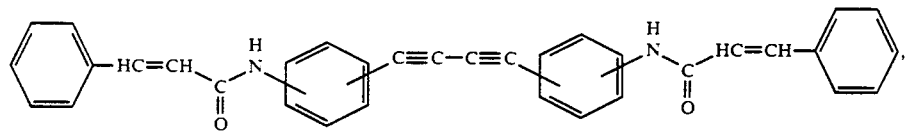

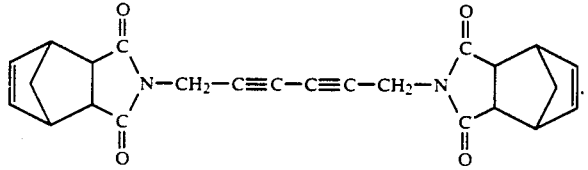

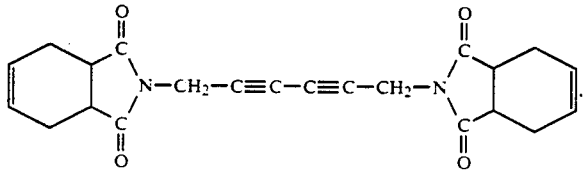

-continued
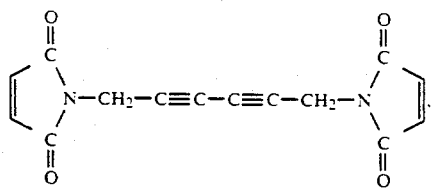
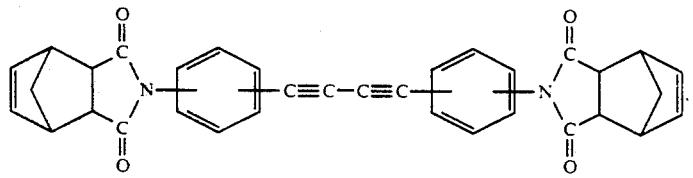
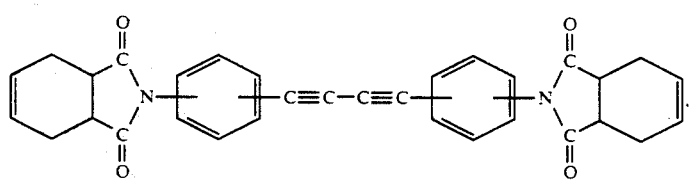
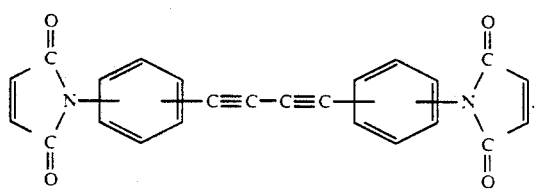
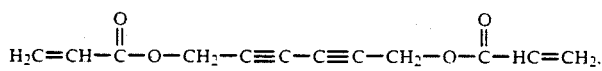
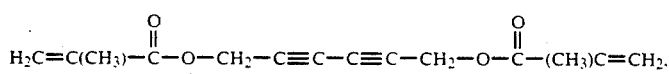
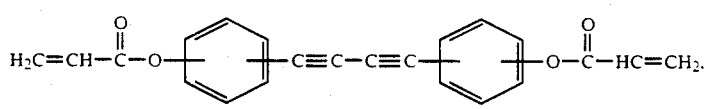
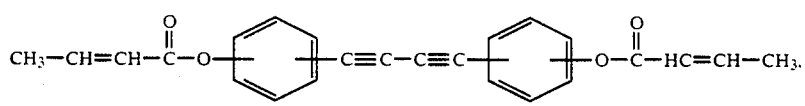
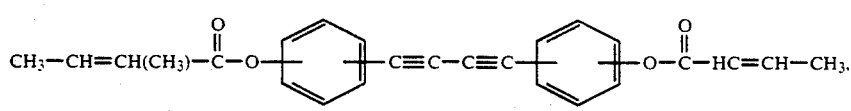
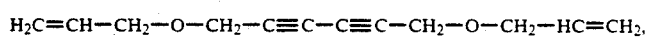
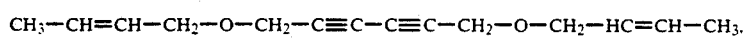
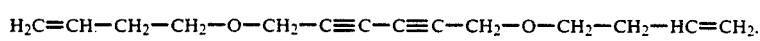
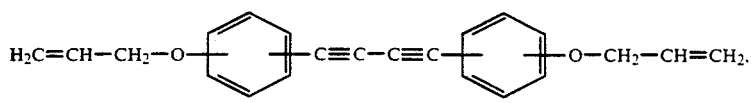

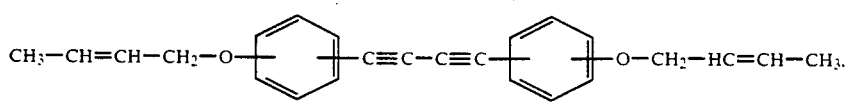
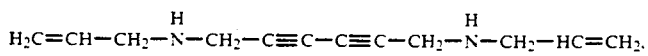
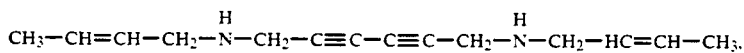
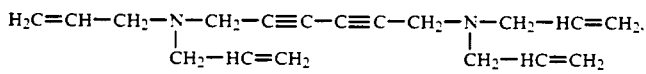
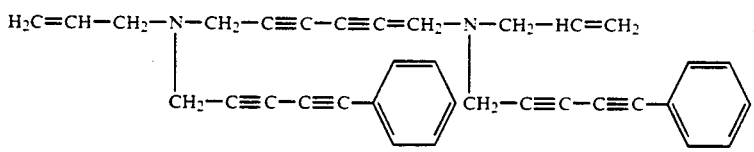
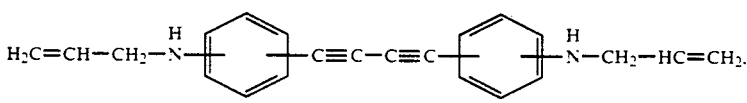
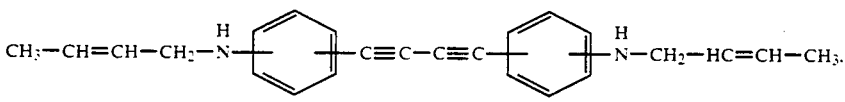
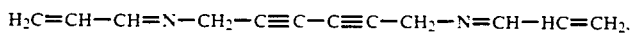
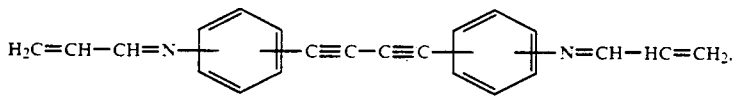
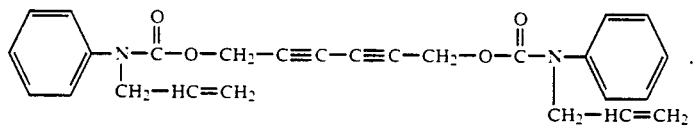
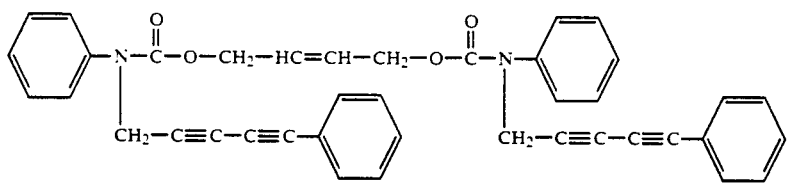
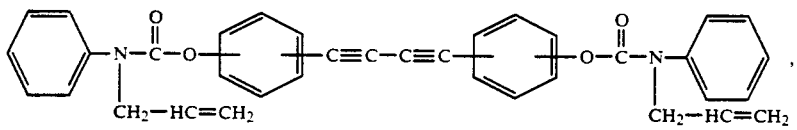
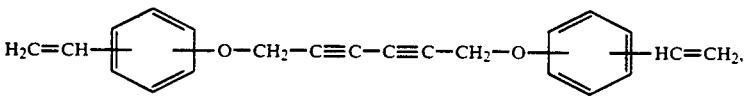
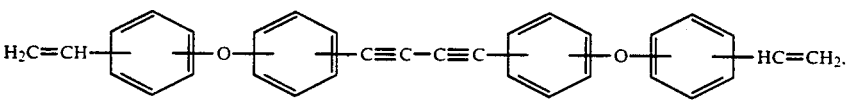

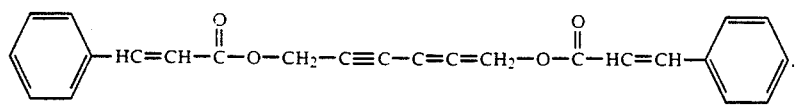
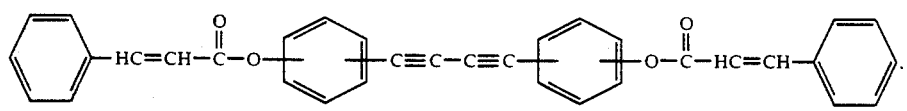
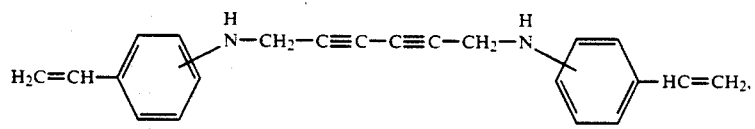
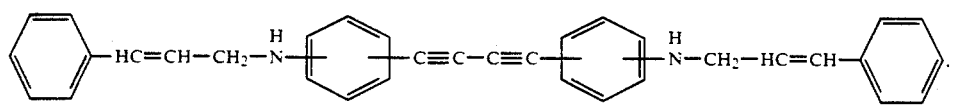
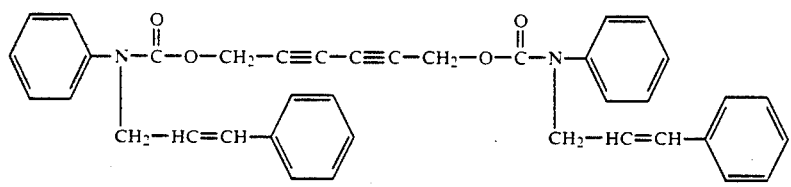
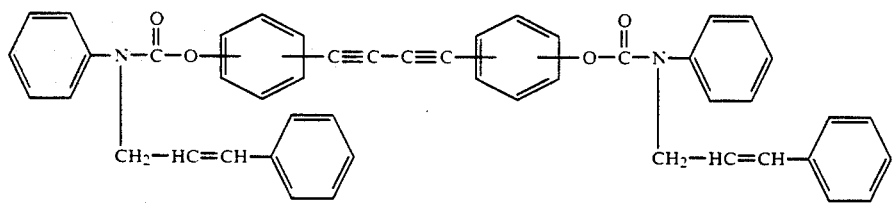
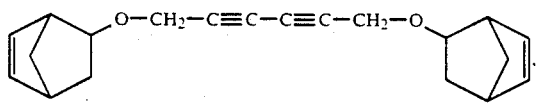
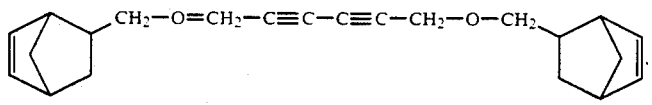
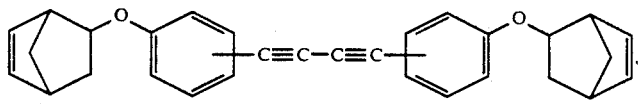
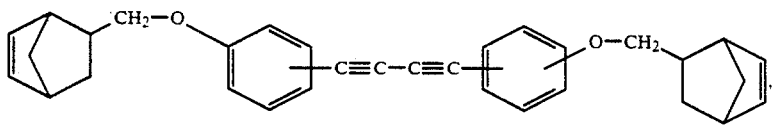
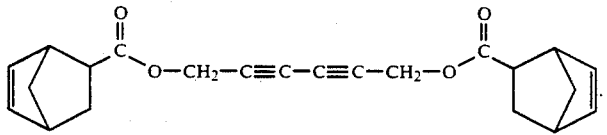

-continued
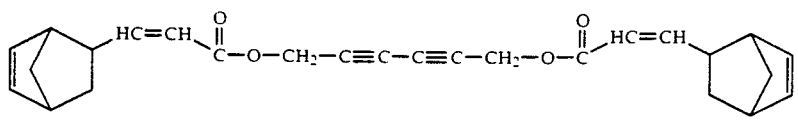
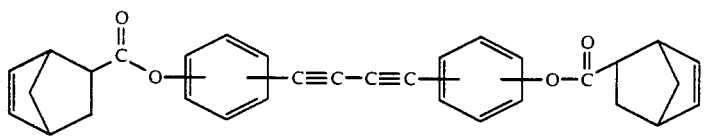
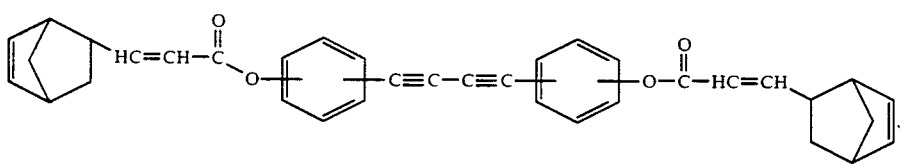
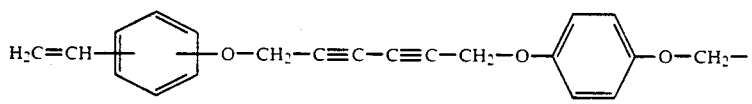
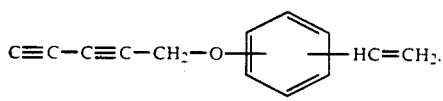
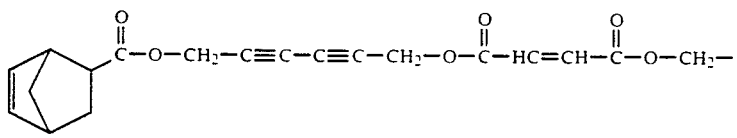
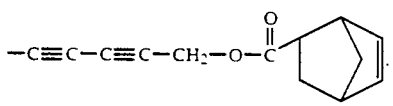
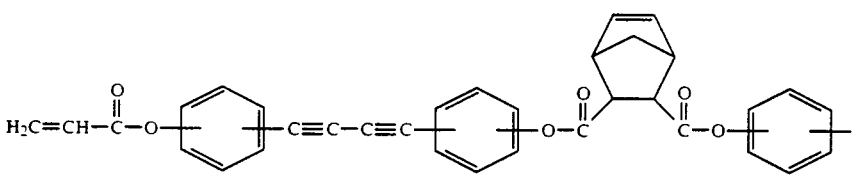
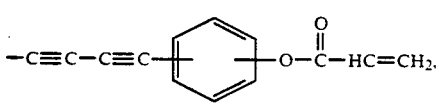
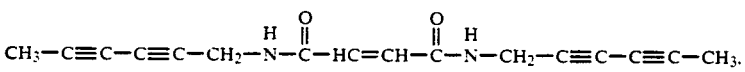
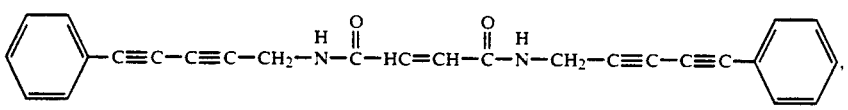
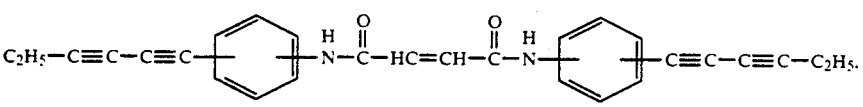

-continued
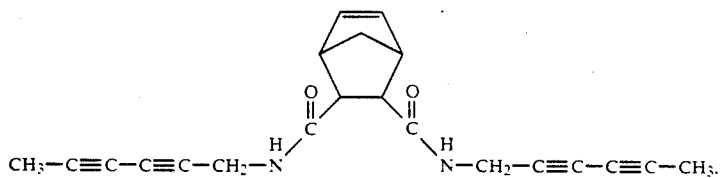
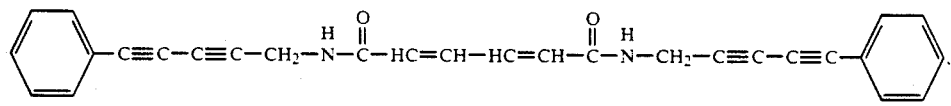
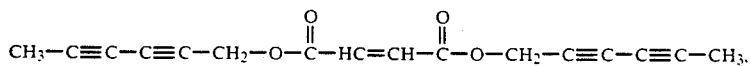
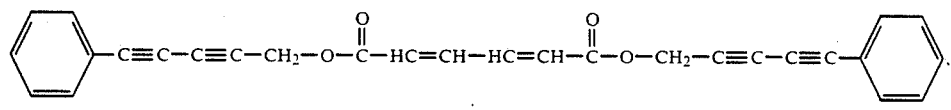
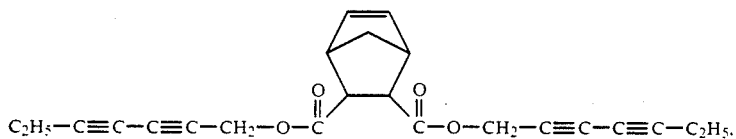
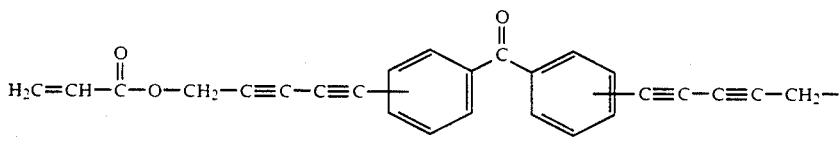
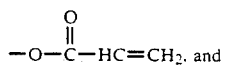
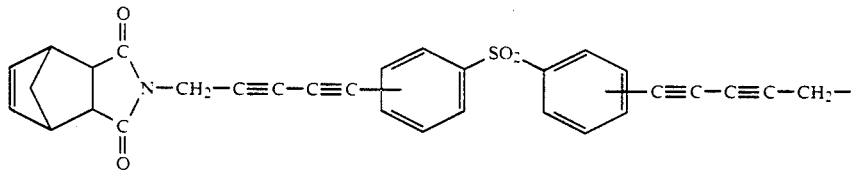
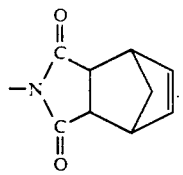
Furthermore, there can be mentioned polymers comprising, for example, the following repeating units:
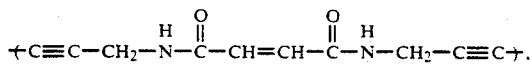
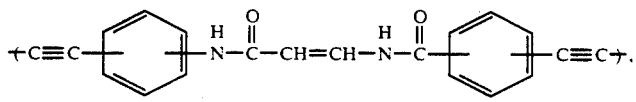
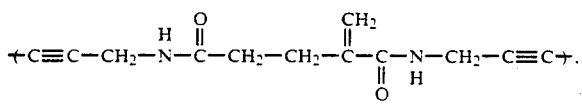

-continued
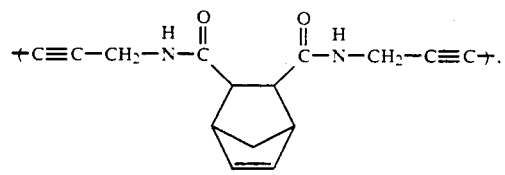
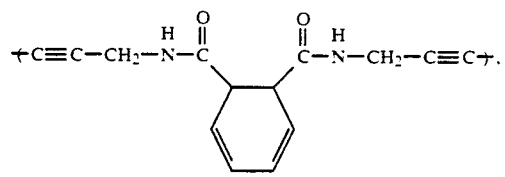
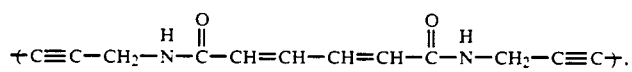
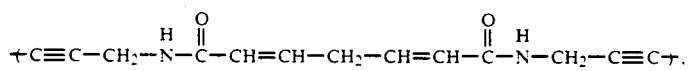
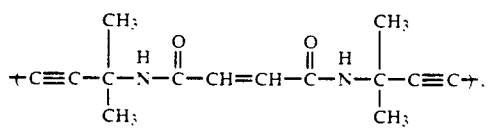
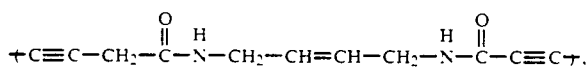
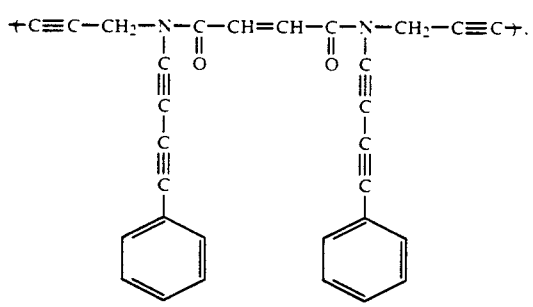
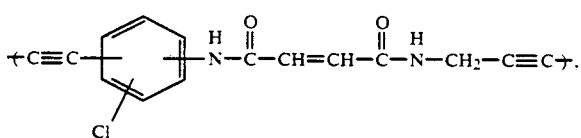
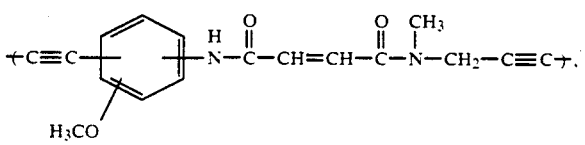

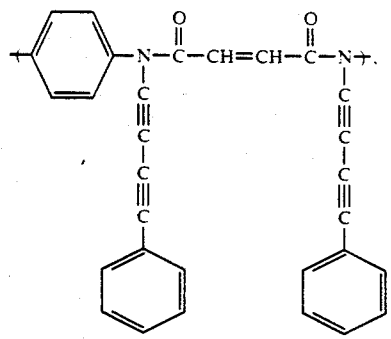

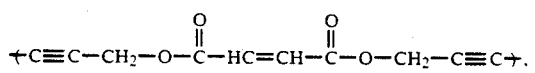

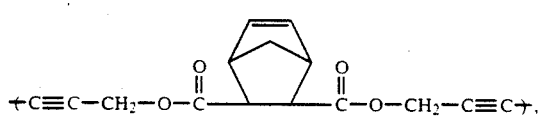

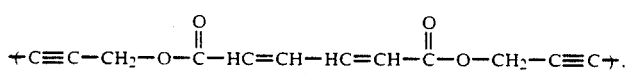

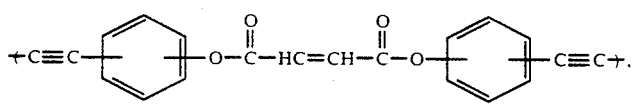

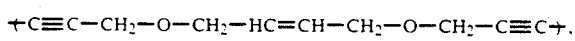

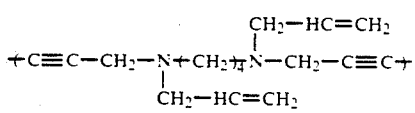

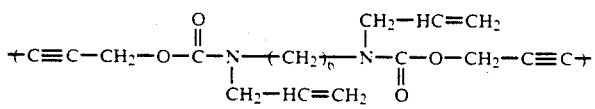

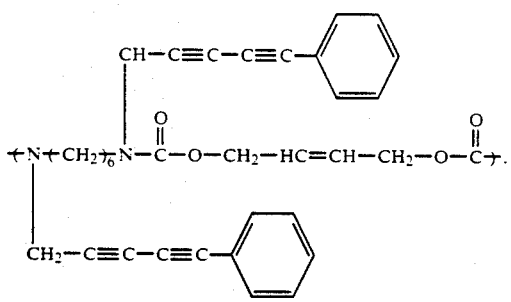

The diacetylene compound of the present invention can be synthesized according to processes developed by modifying or improving known organic synthesis processes.

For example, a diacetylene compound containing an amide bond as the connecting group can be synthesized by polycondensing as the starting material a diamine represented by the formula

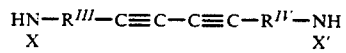

(in which $R^{III}$ and $R^{IV}$ are as defined above and X and X' independently represent a hydrogen atom or an organic group) with a carboxylic acid halide

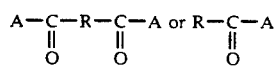

(in which R is an organic group having at least one carbon-to-carbon double bond, and A represents a halogen atom), a carboxylic acid ester

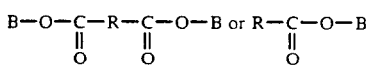

(in which R is as defined above and B represents an organic group) or a carboxylic acid

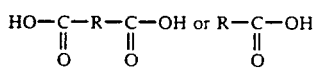

(hereinafter referred to as "process 1"), or by subjecting a diamide

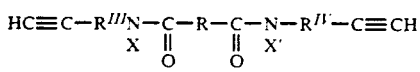

(in which R, $R^{III}$ and $R^{IV}$ are as defined above) to oxidative coupling polymerization in the presence of a metal catalyst such as CuCl (hereinafter referred to as "process 2").

A diacetylene compound having an ester bond as the connecting group can be synthesized by polycondensing a diol HO—$R^{III}$—C≡C—C≡C—$R^{IV}$—OH (in which $R^{III}$ and $R^{IV}$ are as defined above) as the starting material with a carboxylic acid halide

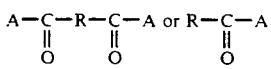

(in which R is as defined above and A represents a halogen atom), a carboxylic acid ester

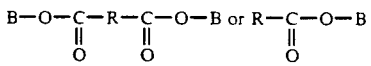

(in which R is as defined above and B represents an organic group) or a carboxylic acid

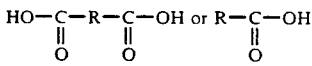

(in which R is as defined above) (hereinafter referred to as "process 1"), or by subjecting

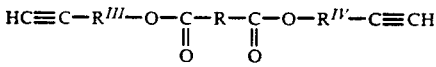

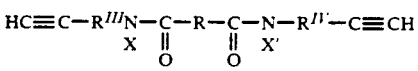

(in which R, $R^{III}$ and $R^{IV}$ are as defined above) to oxidative polymerization in the presence of a metal catalyst such as CuCl (hereinafter referred to as "process 2").

The synthesis process will now be described in detail with reference to a compound having an amide bond.

In the process 1 using, for example, a diamine

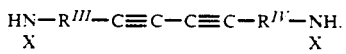

and a carboxylic acid halide

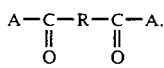

the diamine is dissolved in an alkaline aqueous solution, the carboxylic acid halide is dissolved in a water-immiscible organic solvent and the two solutions are mixed together. Moreover, the intended compound can be synthesized by polycondensing the diamine

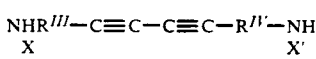

with a carboxylic acid ester

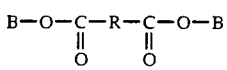

or a carboxylic acid

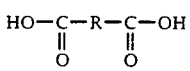

in an organic solvent in the homogeneous system. In this case, if a homogeneous system is formed only by mixing the diamine with the carboxylic acid ester or carboxylic acid, the organic solvent need not be used. This polycondensation in the homogeneous system can also be applied to the carboxylic acid halide.

In the process 2, the intended diacetylene compound can be synthesized, for example, by blowing oxygen into a solution (e.g., in pyridine) of a separately synthesized diamide

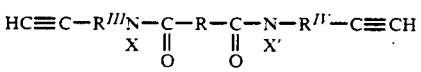

in the presence of a metal catalyst such as CuCl.

In the process 1, the amount of the carboxylic acid halide, carboxylic acid ester or carboxylic acid to the diamine is not particularly critical, but the amount is preferably 0.1 to 2 equivalents.

In the case of the above-mentioned process 1, the kind, concentration and amount of the alkaline aqueous solution are not particularly critical. The reaction temperature and reaction time also are not particularly critical. However, it is generally preferred that the reaction temperature be −20° to 300° C. and the reaction time be 1 minute to 10 hours.

In the oxidative polymerization in the above-mentioned process 2, it is preferred that the amount of the metal catalyst used be 0.01 to 1 molar equivalent to the starting material and the flow rate of oxygen be 10 to 1000 ml/min. Pyridine is preferred as the solvent used for the reaction, and other solvent may be present together with pyridine. The reaction temperature and the reaction time are not particularly critical, but it is generally preferred that the reaction temperature be −20° to 100° C. and the reaction time be 20 minutes to 12 hours.

As the reaction for forming a diacetylene group, there can be adopted the Cadiot-Chodkiewicz coupling process in which a compound having an ethynyl group is brominated and reacted with an other compound having an ethynyl group. For example, this reaction is accomplished by adding an excessive amount of an amine (for example, n-butylamine) and a catalytic amount of cuprous chloride to a solution of a compound having an ethynyl group (for example,

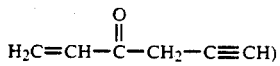

and gradually adding a compound having a brominated ethynyl group (for example,

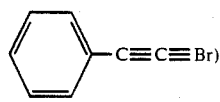

to the mixture with stirring. In order to control the occurrence of a side reaction, it is preferred that the amount of cuprous chloride be 1 to 5 mole %. Moreover, it is necessary that a small amount of hydroxylamine be added.

Furthermore, there may be adopted a process in which an amino bond or a urethane bond is metallized and the metallized compound is reacted with a halide.

The shaped article of the present invention is obtained by shaping and curing the diacetylene compound having at least one carbon-to-carbon double bond. The form of the shaped article is not particularly critical. For example, it can take any of a fibrous form, a filmy form, a sheet- or plate-like form, a membrane-like form, a tubular form, a rod-like form and a powdery form according to need.

For the production of the shaped article of the present invention, there can be adopted various molding methods such as compression molding, injection molding, rotational molding and molding from a solution or dispersion, and the molding method is not particularly critical. Curing is caused at the time of molding or before or after molding. By the term "curing", it is meant that a cured product is neither dissolved in ordinary organic solvents nor fused, and it is generally considered that curing is effected by the crosslinking reaction.

As means for causing curing, there may be adopted application of heat, irradiation with light, compression and irradiation with radial rays or electron beams singly or in combination. Application of heat and compression are simple and effective.

For example, a compressed shaped article excellent in the heat resistance can be obtained by heating a powder of the diacetylene compound without fusion, if necessary under gas compression. Alternatively, the compressed shaped article can be obtained by compressing a powder of the diacetylene compound, if necessary under heating.

Furthermore, a cured film can be obtained by applying or spraying a powder or solution of the diacetylene compound onto a heated article.

Powder of the diacetylene compound of the present invention can be conveniently and effectively cured and molded by adopting heating means together with rotational molding, injection molding, extrusion molding, rolling molding or the like.

In the case where the diacetylene compound of the present invention is a polymer or oligomer, combination of molding into a fiber or film with heat curing or with heat rolling or heat compression is preferred.

In the case where the diacetylene compound of the present invention is highly crystallizable, there may be adopted a process in which a crystal is grown and the crystal is cured by heating or compression at a temperature lower than the melting point.

In producing the cured shaped article of the present invention, appropriate conditions for application of heat, compression or the like are selected according to the properties of the diacetylene compound. For example, there may be adopted a method in which before molding, the differential thermal analysis is carried out to examine the temperature range where curing is effectively caused. The heating temperature is generally room temperature to 400° C. and preferably room temperature to 350° C. In order to shorten the curing molding time in the industrial process, it is most preferred that the heating temperature be 30° to 300° C. However, even if the heating temperature is lower than about 250° C., curing is sufficiently advanced and the shaped article can be easily produced.

Application of pressure is not indispensable but a reduced pressure system may be adopted in a certain method. However, if powder is shaped into a body having a specific form, application of pressure is preferred and is utilized for promotion of curing. Generally, the pressure is at least 0.5 MPa, and the upper limit is not particularly critical and a pressure of up to the upper limit attainable in the industrial static pressure technique may be adopted. Moreover, the impact pressure may be utilized. It is preferred that the pressure be 1 to 1,000 MPa, especially 5 to 700 MPa.

In the production of the shaped article, the diacetylene compound can be mixed with a thermosetting resin, a thermoplastic resin, an inorganic substance, a metal, a carbon material, a stabilizer, a flow modifier, a parting material, a colorant, an ultraviolet absorber, a curing promotor, a curing inhibitor or the like. The form of the shaped article is not limited to a powdery form, but the shaped body may have a sheet-like form, a paper-like form, a fibrous form, a fleecy form, a fibrous form, a granular form, a slice-like form, a plate-like form, a rod-like form or a tubular form according to need.

The cured shaped article of the diacetylene compound according to the present invention has excellent mechanical properties. For example, the elastic modulus is at least 4 GPa, generally 5 to 8 GPa. If the kind of the diacetylene compound and the molding conditions are appropriately selected, an elastic modulus of about 10 GPa can be manifested.

In the present invention, the flexural modulus or the tensile modulus can be adopted as the elastic modulus according to the form of the shaped article. As the standard method for determining the flexural modulus, there can be adopted the method of ASTM D790-66. However, the shaped article of the present invention is not limited to those which have a size (length) sufficient for the measurement according to the method of ASTM D790-66. Accordingly, the following method is adopted for measuring the flexural modulus of a small shaped article.

According to the method for measuring the flexural modulus, which is used in the present invention, the measurement is carried out by using a test specimen having a length of at least 15 mm, a width of 4 mm, and a thickness of 2 mm, at a span (distance between the supports) of 10 mm, a support nose radius of 2R, a loading nose radius of 5R and a crosshead rate of 5 mm/min. The value of the flexural modulus obtained according to this method as slightly smaller than but close to the value obtained according to the method of ASTM D790-66.

The diacetylene compound of the present invention can be cured, for example, at a temperature lower than 300° C., especially a temperature lower than 250° C., and in a certain compound, curing is possible at a temperature lower than 100° C. The obtained shaped article has excellent mechanical properties. In ordinary organic polymers, the flexural modulus is 1 to 3 GPa. On the other hand, the cured shaped article of the present invention has a flexural modulus of at least 4 GPa and generally 5 to 8 GPa. In the case of a shaped article of a certain compound included in the scope of the present invention, a flexural modulus of about 10 GPa is manifested.

The shaped article of the present invention is very useful for electronic materials and precision machine parts.

The present invention will now be described in detail with reference to the following examples that by no means limit the scope of the invention.

EXAMPLE 1

Synthesis of

In 100 ml of a 5N aqueous solution of NaOH was dissolved 0.5 mole of propargylamine, the solution was mixed with a solution of 0.5 mole of acryloyl chloride in chloroform, and the mixture was vigorously stirred at room temperature for 10 minutes. After the reaction was completed, the chloroform layer was separated, and the residue was dried with anhydrous sodium sulfate to obtain

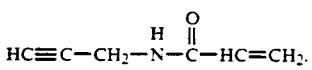

The thus-obtained product was stirred in pyridine in the presence of cuprous chloride as the catalyst at room temperature for 2 hours under bubbling with oxygen at a flow rate of 500 ml/min. After the reaction was completed, the precipitated product was isolated by filtration under suction.

When the product was heated at a temperature-elevating rate of 20° C./min in nitrogen, exothermic phenomenon was observed (namely, curing occurred) at 80° to 100° C. without melting. The elementary analysis values as $C_{12}H_{12}N_2O_2$ were as follows.

Calculated values: C, 66.7%; H, 5.5%; N, 13.0%; O, 14.8%.

Found values: C, 66.6%; J, 5.3%; N, 13.1%; O, 15.0%.

In the IR absorption spectrum, characteristic absorptions were observed at 2170 cm$^{-1}$ (—C≡C—), 1650 cm$^{-1}$(amide bond) and 1580 cm$^{-1}$(amide bond).

The compound was soluble in methanol, ethanol and ethyl acetate.

The product obtained by maintaining this compound at 200° C. for 1 hour in nitrogen was insoluble in methanol, ethanol and ethyl acetate.

EXAMPLE 2

Synthesis of

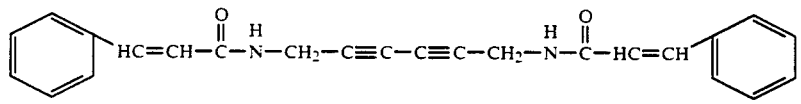

The reaction was carried out in the same manner as described in Example 1 except that cinnamoyl chloride was used instead of acryloyl chloride.

When the product was heated at a temperature-elevating rate of 20° C./min in nitrogen, exothermic phenomenon was observed (namely, curing occurred) at about 100° C. without fusion. The elementary analysis values as $C_{24}H_{20}N_2O_2$ were as follows.

Calculated values: C, 78.3%; H, 5.4%; N, 7.6%; O, 8.7%.

Found values: C, 78.1%; H, 5.6%; N, 7.4%; O, 8.9%.

In the IR absorption spectrum of the compound, characteristic absorptions were observed at 2170 cm$^{-1}$(—C≡C—), 1650 cm$^{-1}$(amide bond) and 1580 cm$^{-1}$(amide bond). The compound was soluble in acetone, methanol, ethanol and ethyl acetate.

When the compound was maintained at 200° C. for 1 hour in nitrogen, the product was insoluble in acetone, methanol, ethanol and ethyl acetate.

EXAMPLE 3

Synthesis of

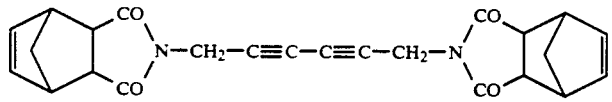

In acetic acid, 0.165 mole (27.06 g) of 5-norbornene-2,3-dicarboxylic anhydride was reacted with 0.165 mole (9.1 g) of propargylamine in acetic acid under reflux. After the reaction was completed, the half of acetic acid was evaporated from the solution, and the reaction mixture was cooled and poured into water. The precipitate was isolated by filtration under suction, and water washing was repeated until the smell of acetic acid disappeared, followed by drying under a reduced pressure (product A). A solution of 16.08 g of the product in pyridine was dropped into a pyridine solution containing 0.08 mole (0.8 g) of cuprous chloride in a flask while bubbling with oxygen. After the reaction was completed, the solution was poured into water and the precipitate was isolated by filtration. Water washing and was repeated, followed by drying under a reduced pressure. A pale yellow powder was obtained. The yield was 87.9% (14 g).

The melting point of the product was 190° to 193° C., and the elementary analysis values as $C_{24}H_{20}O_4N_2$ were as follows.

Calculated values: C, 72.0%; H, 5.0%; N, 7.0%; O, 16.0%.

Found values: C, 72.0%; H, 4.5%; N, 6.8%; O, 16.7%.

In the IR absorption spectrum of the compound, characteristic absorptions were observed at 2170 $cm^{-1}$(—C≡C—) 1770 $cm^{-1}$(5-membered ring imide) and 1720 $cm^{-1}$(5-membered ring imide).

The solubility of the compound in a solvent was excellent. Namely, the compound was soluble in acetone at room temperature and in methanol, ethanol and ethyl acetate under slight heating.

When the compound was heated, melting began at 190° C. and curing began at about 210° C., and the compound was completely cured at about 250° C. Furthermore, when the compound was maintained at 210° C. for 5 minutes, the compound was completely cured. Moreover, at 200° C., curing was completed in 10 minutes. When the thermogravimetric analysis of the cured product was carried out in air, the weight loss was only 1.5% at 450° C. Thus, it was confirmed that the heat resistance was very excellent.

EXAMPLE 4

Synthesis of

In the same manner as described in Example 3, 20 g (77% based on the theoretical value) of a powder of a light yellow color was prepared from 5-norbornene-2,3-dicarboxylic anhydride and aminophenylacetylene obtained according to the process disclosed in Japanese Unexamined Patent Publication No. 54-122,242.

The product was not fused up to 300° C. The elementary analysis values as $C_{34}H_{24}O_4N_2$ were as follows.

Calculated values: C, 77.9%; H, 4.6%; O, 12.2%; N, 5.3%.

Found values: C, 78.0%; H, 5.0%; O, 11.8% N, 5.1%.

In the IR absorption spectrum of the compound, characteristic absorptions were observed at 2145 $cm^{-1}$(—C≡C—), 1770 cm (5-membered ring imide) and 1715 $cm^{-1}$(5-membered ring imide).

When the thermogravimetric analysis of the compound was carried out in air, the weight loss was only 1% at 470° C.

EXAMPLE 5

Synthesis of

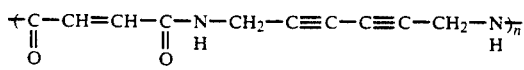

In 200 ml of a 4N aqueous solution of NaOH was dissolved 0.5 mole of $H_2N$—$CH_2$—C≡C—C≡C—$CH_2$-$NH_2$, and 100 ml of a solution of 5 mole of

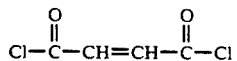

in chloroform was gradually dropped into the alkaline solution at 0° C. After the dropwise addition, white mass was immediately precipitated. The mixture was stirred for 30 minutes to complete the reaction. The formed polymer was isolated by filtration under suction. The yield was 96%. In the IR absorption spectrum (KBr method) of the polymer, characteristic absorptions were observed at 2960 $cm^{-1}$, 1650 $cm^{-1}$ and 1580 $cm^{-1}$.

When differential thermal analysis (DTA) and thermogravimetric analysis (TGA) of the polymer were carried out in a nitrogen current at a temperature-elevating rate of 20° C./min, it was found that decomposition was not caused up to 200° C. The crosslinked polymer obtained by annealing the polymer at 180° C. for 5 hours was not thermally decomposed at 300° C. and thus showed a good heat resistance.

EXAMPLE 6

Synthesis of

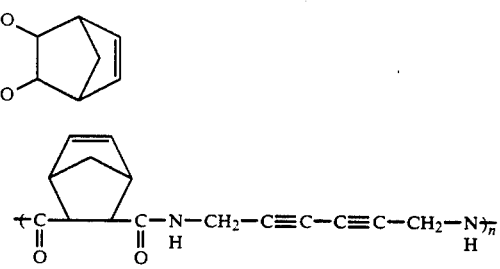

The procedures of Example 5 were repeated in the same manner except that

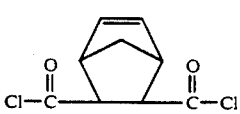

was used instead of

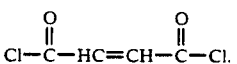

In the IR absorption spectrum (KBr) of the product, characteristic absorptions were observed at 3000 cm$^{-1}$, 1662 cm$^{-1}$ and 1583 cm$^{-1}$. The product was soluble in N-methylpyrrolidone. When the product was heated in nitrogen at a temperature-elevating rate of 20° C./min, exothermic phenomenon was observed at about 100° C. The product was rendered insoluble in N-methylpyrrolidone when maintained at 130° C. for 3 hours.

EXAMPLE 7

Synthesis of

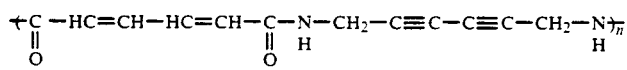

The procedures of Example 5 were repeated in the same manner except that

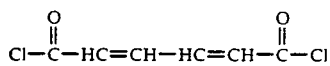

was used instead of

When the product was heated in nitrogen at a temperature-elevating rate of 20° C./min, exothermic phenomenon was observed (namely, curing occurred) at about 90° C. without fusion.

EXAMPLE 8

Synthesis of

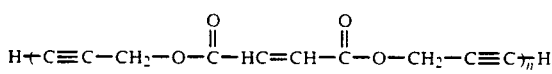

To a mixture of 1.5 moles of propargyl alcohol (HC≡C—CH$_2$—OH) and 1.0 mole of Na$_2$CO$_3$ was dropped 0.5 mole of

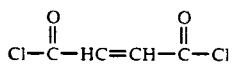

over a period of 10 minutes. The mixture became white mass in about 1.5 hours after the dropwise addition. Water was added to the solid and the precipitate was isolated by filtration under suction. Obtained

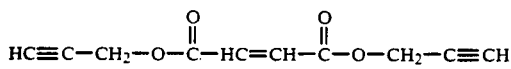

was polymerized in pyridine as a solvent in the presence of cuprous chloride under bubbling with oxygen.

The obtained polymer was soluble in N-methylpyrrolidone and hot dimethylsulfoxide. When the polymer was heated in nitrogen at a temperature-elevating rate of 20° C./min, absorption of heat by fusion was observed at 110° to 140° C. Exothermic phenomenon by curing was observed at about 150° C.

In the IR absorption spectrum, characteristic absorptions were observed at 3287 cm$^{-1}$(terminal H—C≡), 3082 cm$^{-1}$  2130 cm$^{-1}$(—C≡C—) and 1720 cm$^{-1}$(—COO—). The polymer was identified by $^1$H-NMR and $^{13}$C-NMR as well as IR.

The product obtained by maintaining the polymer at 160° C. for 3 hours was insoluble in N-methylpyrrolidone and hot dimethylsulfoxide.

EXAMPLE 9

Synthesis of

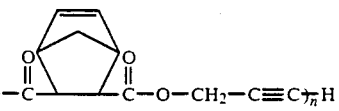

Propargyl alcohol (HC≡C—CH$_2$—OH) was reacted with

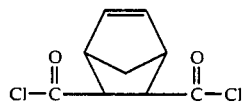

in the presence of triethylamine to obtain

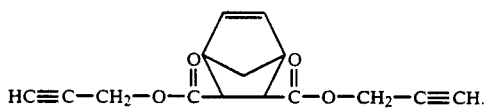

This compound was subjected to the oxidative polymerization in the same manner as in Example 8. The obtained polymer was soluble in tetrahydrofuran. When the polymer was heated at a temperature-elevating rate of 20° C./min in nitrogen, the polymer was softened at about 100° C., and a peak top of exothermic phenomenon appeared at 160° to 170° C. In the IR absorption spectrum, characteristic absorptions were observed at 2163 cm$^{-1}$(—C≡C—) and 1728 cm$^{-1}$(—COO—). The polymer was identified by $^1$H—NMR and $^{13}$C-NMR as well as IR. From the results of gel permeation chromatography (GPC), it was estimated that the molecular weight of the obtained polymer was from several thousands to about 100,000 as calculated as polystyrene. The product obtained by annealing the polymer at 180° C. for 1 hour was insoluble in tetrahydrofuran.

EXAMPLE 10

Synthesis of

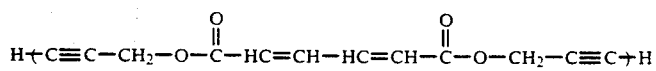

The procedures of Example 8 were repeated in the same manner except that

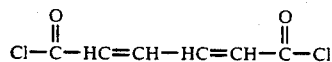

was used instead of

When the obtained polymer was heated in a nitrogen current at a temperature-elevating rate of 20° C./min, exothermic phenomenon by curing reaction was caused at about 150° C. without fusion.

In the IR spectrum of the obtained compound, characteristic absorptions were observed at 3288 cm$^{-1}$(terminal H—C≡),

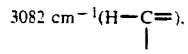

2130 cm$^{-1}$(—C≡C—) and 1720 cm$^{-1}$(—COO—). The compound was identified by IR and elementary analysis.

EXAMPLE 11

Figure 2:
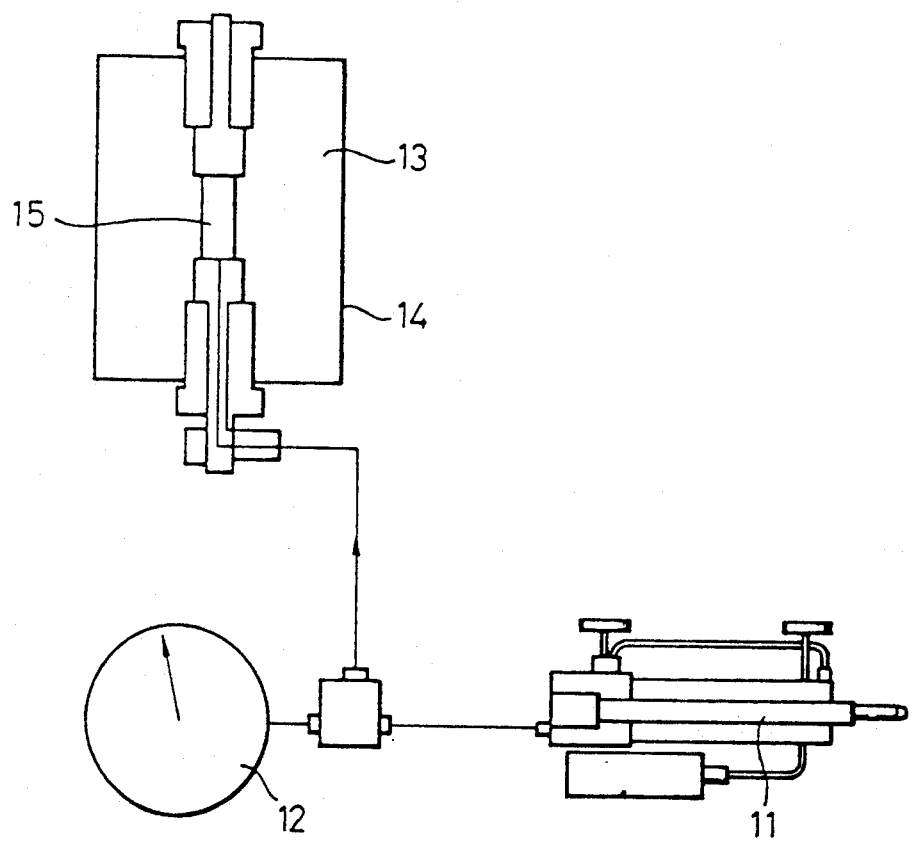
FIG. 2 is a schematic diagram illustrating an isostatic pressure apparatus.

The compound synthesized in Example 1 was molded into a rod-like article by using the molding machine shown in FIG. 1 and the isostatic pressure apparatus shown in FIG. 2. Referring to FIG. 1, reference numeral 1 represents a pushing rod, reference numeral 2 represents a pressing member, reference numeral 3 represents a lid of a cylinder, reference numeral 4 represents an outer cylinder, reference numeral 5 represents an air discharge pipe, reference numeral 6 represents an inner cylinder, reference numeral 7 represents a receiving plug, reference numeral 8 represents a polymeric material, and each of reference numerals 9 and 10 represents an O-ring. Referring to FIG. 2, reference numeral 11 represents a hydraulic pump, reference numeral 12 represents a pressure gauge, reference numeral 13 represents a pressure vessel, reference numeral 14 represents a band heater, and reference numeral 15 represents a high-pressure chamber.

Namely, the compound synthesized in Example 1 was packed in the cylinder 4 of the molding machine shown in FIG. 1, and the inner pressure was reduced by a vacuum pump. Subsequently, the molding machine was placed on a hydraulic press and compression molding was carried out under a pressure of 30 MPa for 5 minutes at 30° C. Then, by using the isostatic pressure apparatus shown in FIG. 2, the molded article was treated under conditions shown in Table 1. The elastic modulus of the molded article was measured. The obtained results are shown in Table 1.

TABLE 1

| Pressure (MPa) | Temperature (°C.) | Time (hours) | Elastic Modulus (GPa) |
|---|---|---|---|
| 50 | 23 | 1 | 9.4 |
| 100 | 23 | 1 | 10.0 |
| 300 | 23 | 1 | 11.2 |
| 300 | 50 | 1 | 11.3 |
| 300 | 100 | 1 | 13.2 |
| 650 | 23 | 1 | 12.0 |
| 650 | 50 | 1 | 12.4 |
| 650 | 100 | 1 | 14.0 |
| 650 | 150 | 1 | 14.3 |

EXAMPLE 12

A molded article shown in Table 2 was obtained by treating the compound of Example 2 in the same manner as in Example 11.

TABLE 2

| Pressure (MPa) | Temperature (°C.) | Time (hours) | Elastic Modulus (GPa) |
|---|---|---|---|
| 50 | 23 | 1 | 7.2 |
| 100 | 23 | 1 | 8.1 |
| 300 | 23 | 1 | 8.6 |
| 300 | 50 | 1 | 8.9 |
| 300 | 100 | 1 | 10.1 |
| 650 | 23 | 1 | 8.9 |
| 650 | 50 | 1 | 9.2 |
| 650 | 100 | 1 | 10.5 |
| 650 | 150 | 1 | 11.6 |

EXAMPLE 13

A molded article shown in Table 3 was obtained by treating the compound of Example 3 in the same manner as in Example 11.

TABLE 3

| Pressure (MPa) | Temperature (°C.) | Time (hours) | Elastic Modulus (GPa) |
|---|---|---|---|
| 50 | 200 | 1 | 6.6 |
| 100 | 200 | 1 | 7.2 |

EXAMPLE 14

A molded article shown in Table 4 was obtained by treating the compound of Example 4 in the same manner as in Example 11.

TABLE 4

| Pressure (MPa) | Temperature (°C.) | Time (hours) | Elastic Modulus (GPa) |
|---|---|---|---|
| 650 | 190 | 5 | 7.2 |

EXAMPLE 15

A molded article shown in Table 5 was obtained by treating the compound of Example 5 in the same manner as in Example 11.

TABLE 5

| Pressure (MPa) | Temperature (°C.) | Time (hours) | Elastic Modulus (GPa) |
|---|---|---|---|
| 400 | 150 | 2 | 10.8 |
| 650 | 100 | 1 | 15.0 |

TABLE 5-continued

| Pressure (MPa) | Temperature (°C.) | Time (hours) | Elastic Modulus (GPa) |
|---|---|---|---|
| 650 | 150 | 2 | 15.2 |
| 650 | 200 | 1 | 16.6 |

EXAMPLE 16

A molded article shown in Table 6 was obtained by treating the compound of Example 6 in the same manner as in Example 11.

TABLE 6

| Pressure (MPa) | Temperature (°C.) | Time (hours) | Elastic Modulus (GPa) |
|---|---|---|---|
| 200 | 100 | 2 | 7.3 |
| 200 | 150 | 2 | 9.6 |
| 200 | 200 | 2 | 10.4 |
| 650 | 100 | 2 | 8.2 |
| 650 | 150 | 2 | 11.0 |
| 650 | 200 | 2 | 12.1 |

EXAMPLE 17

A molded article shown in Table 7 was obtained by treating the compound of Example 7 in the same manner as in Example 11.

TABLE 7

| Pressure (MPa) | Temperature (°C.) | Time (hours) | Elastic Modulus (GPa) |
|---|---|---|---|
| 200 | 100 | 2 | 10.0 |
| 200 | 150 | 2 | 12.8 |
| 200 | 200 | 2 | 13.9 |
| 650 | 100 | 2 | 13.9 |
| 650 | 150 | 2 | 14.3 |
| 650 | 200 | 2 | 15.6 |

EXAMPLE 18

A molded article shown in Table 8 was obtained by treating the compound of Example 8 in the same manner as in Example 11.

TABLE 8

| Pressure (MPa) | Temperature (°C.) | Time (hours) | Elastic Modulus (GPa) |
|---|---|---|---|
| 30 | 100 | 1 | 8.6 |
| 30 | 150 | 1 | 10.2 |
| 30 | 180 | 1 | 11.8 |
| 200 | 100 | 1 | 9.2 |
| 200 | 150 | 1 | 13.2 |
| 200 | 180 | 1 | 14.0 |
| 650 | 100 | 1 | 11.5 |
| 650 | 150 | 1 | 18.3 |
| 650 | 180 | 1 | 20.7 |

EXAMPLE 9

A molded article shown in Table 9 was obtained by treating the compound of Example 9 in the same manner as in Example 11.

TABLE 9

| Pressure (MPa) | Temperature (°C.) | Time (hours) | Elastic Modulus (GPa) |
|---|---|---|---|
| 200 | 100 | 1 | 7.4 |
| 200 | 150 | 1 | 9.8 |
| 200 | 200 | 1 | 10.5 |
| 650 | 100 | 1 | 8.4 |
| 650 | 150 | 1 | 11.3 |

TABLE 9-continued

| Pressure (MPa) | Temperature (°C.) | Time (hours) | Elastic Modulus (GPa) |
|---|---|---|---|
| 650 | 200 | 1 | 12.4 |

EXAMPLE 20

A molded article shown in Table 10 was obtained by treating the compound of Example 10 in the same manner as in Example 11.

TABLE 10

| Pressure (MPa) | Temperature (°C.) | Time (hours) | Elastic Modulus (GPa) |
|---|---|---|---|
| 200 | 100 | 1 | 8.9 |
| 200 | 150 | 1 | 12.8 |
| 200 | 180 | 1 | 13.6 |
| 650 | 100 | 1 | 11.2 |
| 650 | 150 | 1 | 16.5 |
| 650 | 180 | 1 | 18.7 |

We claim:

1. A diacetylene compound consisting of the structural units:

(a) at least one member selected from the group consisting of a diacetylene derivative of formulae (I):

$$R^{I}-C\equiv C-C\equiv C-R^{II}- \quad (I)$$

and a diacetylene derivative of formula (II):

$$-R^{III}-C\equiv C-C\equiv C-R^{IV}- \quad (II)$$

wherein $R^{I}$ represents a monovalent hydrocarbon group selected from the group consisting of —CH$_3$, —C$_2$H$_5$ and

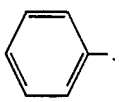

and $R^{II}$, $R^{III}$ and $R^{IV}$ independently represent a divalent hydrocarbon group selected from the group consisting of

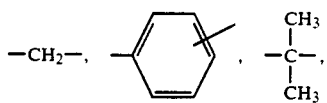

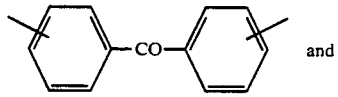 and

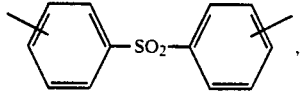, (b) at least one organic group having at least one non-aromatic carbon-to-carbon double bond, selected from the group consisting of:

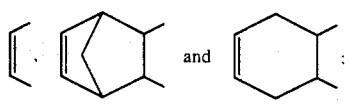 and 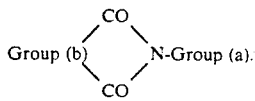

and (c) at least one connecting group bonded directly to an open valence of each of said structural units (a) and (b), said connecting group (c) being selected from the group consisting of:

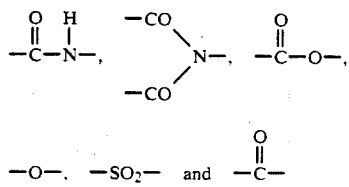

wherein at least one (c) group is

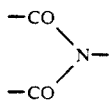

in the form of:

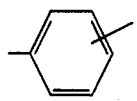

2. A diacetylene compound as set forth in claim 1, wherein the molar ratio of the diacetylene group-containing organic group (a) represented by the general formula (I) or (II) to the double bond-containing organic group is in the range of from 0.2 to 5.

3. A diacetylene compound as set forth in claim 1, wherein $R^{II}$, $R^{III}$ and $R^{IV}$ in the formulae independently represent —$CH_2$— or

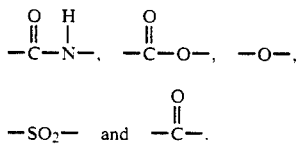

4. A diacetylene compound as set forth in claim 1, wherein said diacetylene compound has the following structure:

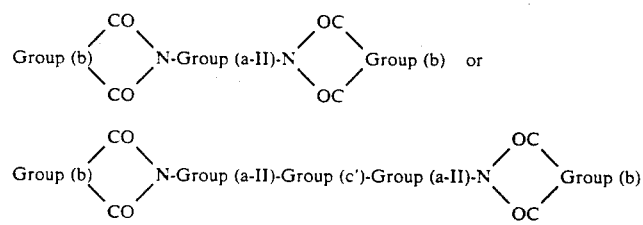

wherein Group (c') is selected from the group consisting of:

$$-\overset{O}{\underset{\|}{C}}-\overset{H}{\underset{|}{N}}-, \quad -\overset{O}{\underset{\|}{C}}-O-, \quad -O-,$$

$$-SO_2- \quad \text{and} \quad -\overset{O}{\underset{\|}{C}}-.$$

* * * * *